United States Patent [19]

Kavadias et al.

[11] 4,003,922

[45] Jan. 18, 1977

[54] SYNTHESIS OF CIS-1,4-CYCLOHEXADIENE DIOXIDE

[75] Inventors: Gerry Kavadias, St-Lambert; Bernard Belleau, Westmount, both of Canada

[73] Assignee: Bristol-Myers Company, New York, N.Y.

[22] Filed: Feb. 10, 1976

[21] Appl. No.: 656,919

Related U.S. Application Data

[62] Division of Ser. No. 634,396, Nov. 24, 1975.

[52] U.S. Cl. .................. 260/348.5 L; 260/348 C; 536/17; 536/10; 260/307 C
[51] Int. Cl.² ...................................... C07D 301/14
[58] Field of Search ............................ 260/348.5 L

[56] References Cited

OTHER PUBLICATIONS

Craig et al., Jour. Org. Chem. (1967), vol. 32, pp. 3743–3749.

Primary Examiner—Norma S. Milestone
Attorney, Agent, or Firm—Richard R. Lloyd

[57] ABSTRACT

Cis-1,4-cyclohexadiene dioxide is a valuable intermediate useful in the preparation of totally synthetic aminoglycosides. An example of such an aminoglycoside is 5-deoxykanamycin A.

3 Claims, No Drawings

SYNTHESIS OF CIS-1,4-CYCLOHEXADIENE DIOXIDE

CROSS-REFERENCE TO RELATED APPLICATIONS

This application is a divisional application of a copending application Ser. No. 634,396, filed Nov. 24, 1975.

BACKGROUND OF THE INVENTION

1. Field of the Invention:

This invention relates to the synthesis of cis-1,4-cyclohexadiene dioxide, said compound being useful in the total synthesis of aminoglycosides.

2. Description of the Prior Art:

A. Tetsuo Suami et al, *J. Org. Chem.*, 40, 547 (1975) describe the synthesis of four position isomers of dideoxystreptamine.

B. R. T. Testa et al, *The Journal of Antibiotics* 27, 917 (1974), describe the fermentation of aminoglycosides possessing a 2,5-dideoxystreptamine moiety when 2,5-dideoxystreptamine was added to the fermentation media as a precursor.

C. The kanamycins are known antibiotics described in Merck Index, 8th ed., pp. 597–598. Kanamycin A is a compound having the formula

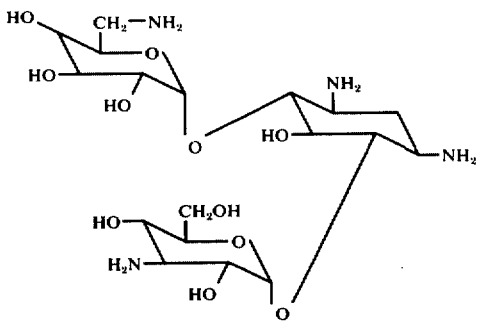

D. T. W. Craig et al, J. Org. Chem., 32, 3743 (1967), reported that bis-epoxidation of 1,4-cyclohexadiene with perbenzoic acid or monoperphthalic acid produced exclusively the trans-epoxide, whereas bis-epoxidation with m-chloroperbenzoic acid or peracetic acid produced a 2:1 mixture of trans- and cis-epoxides respectively. They further reported the cis-epoxide could not be separated from the mixture due to its tendency to form a 1:1 crystalline complex with the trans-epoxide.

SUMMARY OF THE INVENTION

A new process for the preparation of cis-1,4-cyclohexadiene dioxide, having the formula

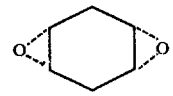

4 has been discovered, which process comprises treating 1,4-cyclohexadiene with m-chloroperbenzoic acid to produce predominantly cis-1,4-cyclohexadiene dioxide.

COMPLETE DISCLOSURE

This invention relates to the total synthesis of 5-deoxyaminoglycosides, such as 5-deoxykanamycin A, said compounds being prepared via the new and novel dextrorotatory and levorotatory isomers of the compound having the formula

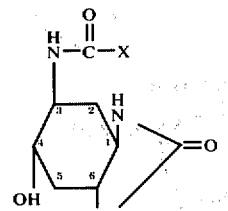

I in which X is OR or R wherein R is (lower)alkyl, $CF_3$ or a group having the formula $-(CH_2)_n$

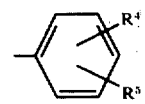

in which $n$ is an integer of 0 to 4 inclusive and $R^4$ and $R^5$ are alike or different and each is H, Cl, Br, I, F, (lower)alkyl, (lower)alkoxy or $NO_2$; or an acid addition salt thereof.

The intermediate compounds I are prepared as illustrated by Chart I.

CHART I

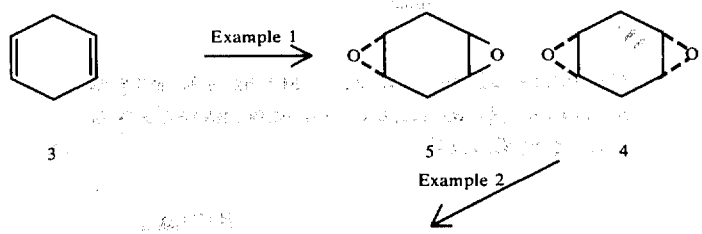

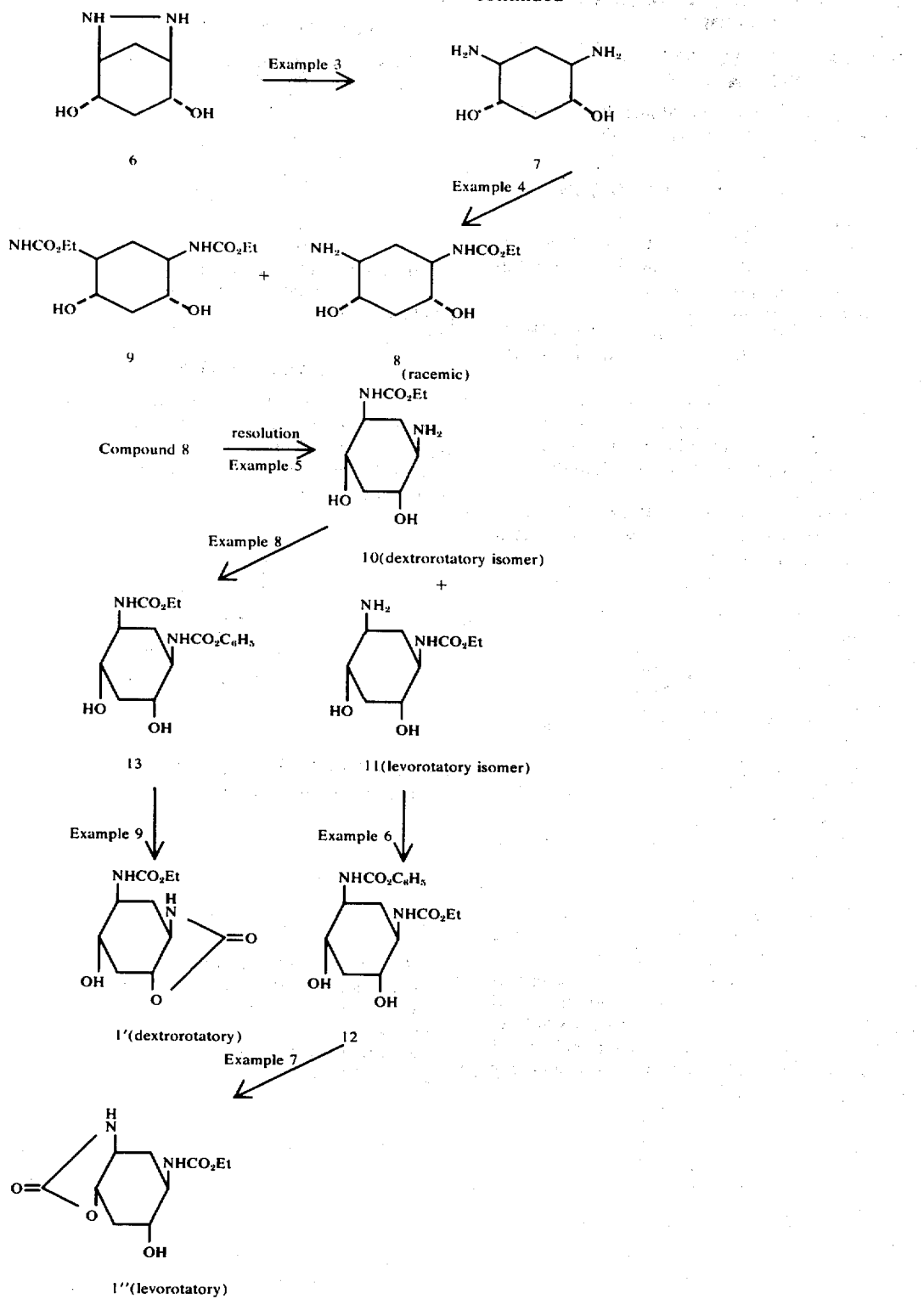
The intermediates 1' and 1" are used to prepare 5-deoxyaminoglycosides, e.g., 5-deoxykanamycin A, as illustrated by Chart II.
CHART II -continued
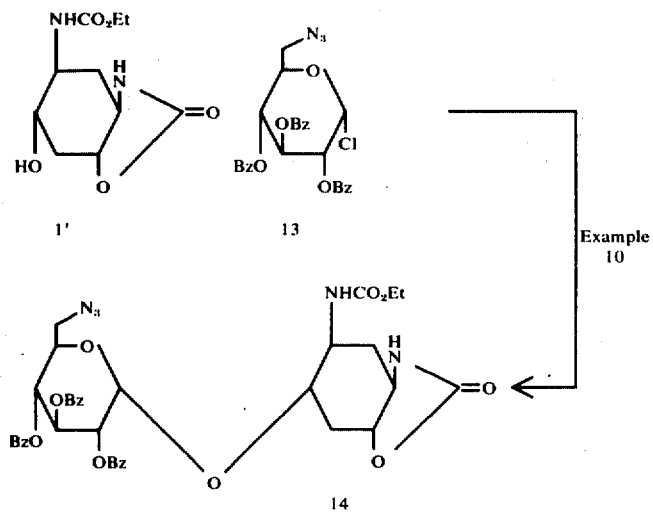
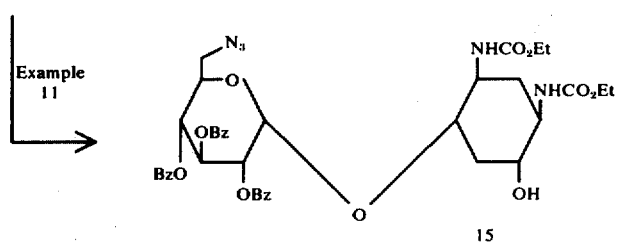
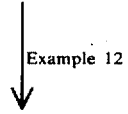
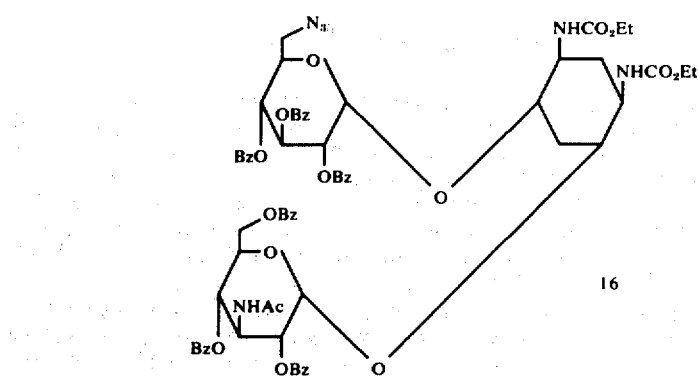

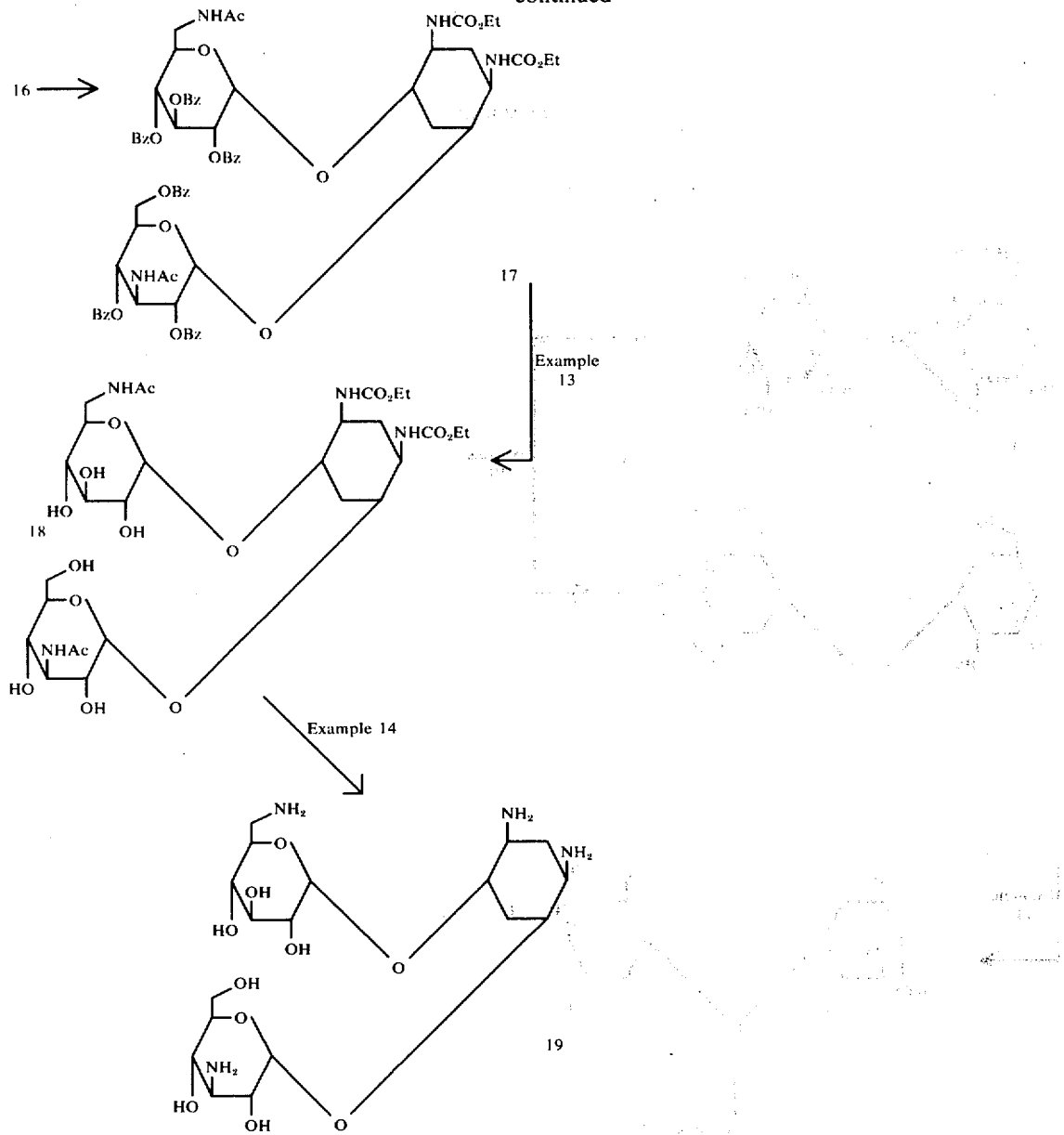

The key intermediate compounds in our synthetic approach are the optical isomers I' and I''. Compounds I' and I'' have all the functional groups protected except the 4- and the 6-OH, respectively. It is, therefore, possible by using the proper isomer to introduce one aminosugar either at the 4- or 6-position of the 2,5-dideoxystreptamine molecule. The position of the attachment of the aminosugar is expected to be of importance for antibiotic activity, since in the aminoglycosides possessing a 2-deoxystreptamine, the positional isomers greatly differ in antibiotic activity. For example, neamine, which is 4-0-(2,6-dideoxy-2,6-diamino-α-D-glucopynanosyl)-2-deoxystreptamine is biologically active whereas the 6-0-isomer is not. After glycosidation of the free OH in I' or I'', the other OH can be de-protected and functionalized by either an aminosugar or another functional group. As an illustration, the synthesis of 5-deoxykanamycin A is described in the examples 11-15.

In the process for the preparation of compounds I, a new and novel process for the preparation of cis-1,4-cyclohexadiene dioxide (4) was found, said process being taught in the literature to be unworkable [see Craig, Harvey and Berchtold, J. Org. Chem. 32, 3743 (1967)].

This literature reference, page 3744, column 1, teaches that the treatment of 1,4-cyclohexadiene with excess perbenzoic acid or monoperphthalic acid gave rise to only the trans-epoxide and that treatment of 1,4-cyclohexadiene with excess peracetic acid gives rise to a 2:1 mixture of the trans and cis epoxide, respectively, and that it was difficult to isolate the pure cis-epoxide from the direct bis-epoxidation of the diene primarily owing to the tendency of the bis cis and trans epoxides to form a crystalline 1:1 complex.

Contrary to this literature report, we have found that cis-1,4-cyclohexadiene dioxide can be prepared directly from 1,4-cyclohexadiene in excellent yields by the direct oxidation of 1,4-cyclohexadiene with m-chloroperbenzoic acid in a temperature range of about −10° C. to about +35° C.

We have found that direct epoxidation of 1,4-cyclohexadiene with m-chloroperbenzoic acid in methylene chloride produced a mixture of cis and trans-epoxides in 90% yield, in which, contrary to the published report, the cis-epoxide was the major isomer. The ratio of the two epoxides; cis v. trans was slightly dependent on the temperature of the reaction. At 0° C. and 25° C., the ratio was 70:30 and 63:37 respectively. We also found that the separation of the isomers was easily accomplished by the continuous extraction of an aqueous solution of the mixture with petroleum ether (essentially n-hexane) or by several extractions of the aqueous solution with ether. The trans-epoxide was extracted by the organic solvent. The cis-epoxide remained in the aqueous solution. The cis-epoxide was recovered from the aqueous solution in approximately 95% purity.

A preferred embodiment of the present invention is the process for the preparation of the compound having the formula

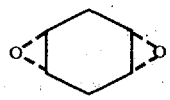

4 which process comprises the step of oxidizing 1,4-cyclohexadiene with an excess of an oxidizing agent selected from the group consisting of peracetic acid, m-chloroperbenzoic acid, trifluoroperacetic acid, perbenzoic acid, monoperphthalic acid and monotereperphthalic acid in a temperature range of about −10° C. to about +35° C.

A more preferred embodiment is the process for the preparation of cis-1,4-cyclohexadiene dioxide, which process comprises oxidizing 1,4-cyclohexadiene with an oxidizing agent selected from the group consisting of peracetic acid, m-chloroperbenzoic acid, trifluoroperacetic acid, perbenzoic acid, monoperphthalic acid and monotereperphthalic acid in a ratio of about 1 mole of diene per two to three moles of peracid in a reaction inert organic solvent selected from the group consisting of methylene chloride, dichloroethane, chloroform, benzene, hexane, toluene, diethylether and dioxane in a temperature range of about −10° C. to about +35° C. with stirring for at least 3 hours.

A more preferred embodiment is the process for the preparation of cis-1,4-cyclohexadiene dioxide, which process comprises oxidizing 1,4-cyclohexadiene with m-chloroperbenzoic acid in methylene chloride in a ratio of about 1 mole of diene per two moles of m-chloroperbenzoic acid at about 0° C. to about +10° C. for at least 3 hours with stirring.

For the purpose of this disclosure, the term (lower)alkyl shall mean a straight or branched chain alkyl group having 1 to 6 carbon atoms. The term (lower)alkoxy shall have a similar meaning, i.e., 1 to 6 carbon atoms.

All melting points are expressed in degrees Centigrade.

EXAMPLE 1 cis and trans-1,4-Cyclohexadiene Dioxide (4,5)

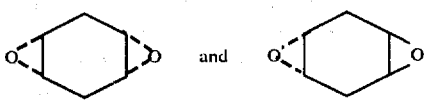

4          5

1. Into a 3-liter, 3-neck flask fitted with mechanical stirrer, dropping funnel and thermometer, was added 335 g of m-chloroperbenzoic acid (1650 mmole) (Aldrich Chemicals, 85% purity) and 1600 ml $CH_2Cl_2$ (dried over molecular sieves) and the suspension stirred and cooled in an ice-bath. A solution of 64.2 g (800 mmole) 1,4-cyclohexadiene (Aldrich, 97% purity) in 170 ml $CH_2Cl_2$ was added dropwise and at such a rate as to keep the inside temperature at 4°–6° C. After the addition, (1½ – 2 hrs.), stirring was continued at the above temperatures for 8 hrs. and at room temperature overnight (14 hrs.). The mixture was filtered and the cake washed with $CH_2Cl_2$ (2 × 150 ml). The combined filtrate and washings were vigorously stirred with an aqueous solution of 20% $Na_2SO_3$ (100 ml) to decompose excess the peracid. After stirring at room temperature for 1 hour, the organic phase was separated and the aqueous phase extracted with $CH_2Cl_2$ until all the epoxide was extracted (8 × 50 ml). The combined $CH_2Cl_2$ extracts were stirred wih 100 g calcium hydroxide at room temperature for 3 hours to remove m-chlorobenzoic acid. The mixture was filtered and the solids washed with $CH_2Cl_2$. The combined filtrate and washings were evaporated to dryness (rotatory evaporator at 40° C) to give 85.0 g (95%) of crude product as a syrup that crystallizes on standing. TLC (thin layer chromatography) on silica plates with ether, (developed with $HClO_4$ or $H_2SO_4$) show two spots with Rf 0.1 (cis-epoxide) and 0.5 (trans-epoxide). NMR shows the mixture to contain about 70% cis and 30% trans-epoxides. In another experiment carried out at room temperature overnight, the composition of the mixture was 63% cis and 37% trans.

2. Separation of the Two Epoxides. Method A

The above crude product (85.0 g) was dissolved in warm water (100 ml) and filtered to remove some insoluble matter (2.5 g). This material seems to be calcium m-chloroperbenzoate. NMR (Nuclear Magnetic Resonance) analysis shows only aromatic protons, it gives the iodine test very slowly, it explodes when heated, it leaves a residue on burning, and it is not soluble in EtOH (whereas the m-chloroperbenzoic acid is soluble). The aqueous solution was placed in a separatory funnel and extracted with an equal volume of ether (100 ml). The ether phase was transferred to a second funnel containing 100 ml water and after shaking, the ether phase was removed. This process was repeated ten times (10 × 100 ml). The combined ether extracts after drying were evaporated to dryness (at 40° C) to give 22.5 g solids shown by NMR to contain about 80% trans and 20% cis-oxides. Recrystallization from EtOH twice (20 ml) gave 14.5 g (17% based on 3) trans-epoxide 5; m.p. 108°–109°. (Reported, 106.5°–107.5°).

The mother liquor, after evaporation to dryness gave 8.0 g syrup which was kept for recycling. The aqueous phases from the two funnels were combined (200 ml). NaCl was added to avoid emulsions and extracted with 70 ml portions of $CH_2Cl_2$ until TCL of the aqueous phase showed complete removal of this compound (10 times). The $CH_2Cl_2$ extracts were combined, dried and evaporated at 40° C to give 52.5 g solid material shown by NMR to contain 92% cis-epoxide and 8% trans-epoxide. This product could be used without further purification in the reaction with hydrazine. When pure cis-oxide was required, the crude product was dissolved by boiling with 750 ml petroleum ether (b.p. 90°–120°), ether (50 ml) was added and allowed to crystallize first at room temperature and then at ice temperature to give 38.5 g.; m.p. 59°–60°. The mother liquor from this recrystallization, after evaporation to dryness (40° C), was dissolved with 250 ml boiling petroleum ether, diluted with 50 ml ether and allowed to crystallize first at room temperature and then at 0° C to give 6.5 g., m.p. 59°–60°. The two crops combined were 45.0 g (52% yield based on I). Reported m.p. 59°–60°.

3. Method B

The crude product from another run, 43.0 g was dissolved with water (200 ml) and filtered to remove some insoluble matter. The aqueous solution was adjusted to pH 7.0 with $NaHCO_3$ and extracted continuously with petroleum ether (b.p. 39°–47°). After 18 hrs., the petroleum ether solution was evaporated to dryness to give 15.5 g solid material shown by NMR (nuclear magnetic resonance) to be a mixture of 60% of trans- and 40% cis-epoxides. Fresh petroleum ether was added and extraction continued for 4 hrs. more. After drying and evaporation, a residue 1.3 g was left shown by NMR to contain 22% trans- and 78% cis-oxide. The solids above (15.5 g) was recrystallized twice from EtOH (2 ml/g) to give 8.0 g trans-oxide; m.p. 108°–109°.

The aqueous phase was extracted continuously with ether for 48 hrs. (or repeatedly with $CH_2Cl_2$ as described in Method A). The extracts after drying and evaporation yielded 22.0 g solid material shown by NMR to contain 95–98% cis-epoxide and 2–5% transisomer. When pure material was required, it was recrystallized as described above in Method A.

EXAMPLE 2

6,7-Diazabicyclo[3.2.1]octane-(2S,4R)-diol (6).

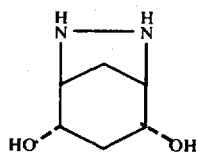

A solution of 17.2 g (153.5 mmole) of the cis-epoxide (4) and 6.6 g (206 mmole) anhydrous hydrazine in 100 ml dry EtOH was refluxed with stirring under nitrogen. After 1 hour refluxing, a crystalline precipitate started to form. The progress of the reaction was followed by TLC (silica, 5% EtOH in ether, sprayed with $HClO_4$). After 10–12 hrs., the spot for 4 (Rf 0.40) disappeared and a new spot with Rf O (6) appeared. After refluxing for 17 hrs., the reaction mixture was cooled in ice and the crystalline product filtered and dried to give 17.5 g (79.5%) 6; m.p. 180°–190° (dec.). The mother liquor was evaporated to dryness and the residue was dissolved with ethanol (35 ml) and left in the refrigerator overnight. The crystalline precipitate was filtered to give 1.0 g 6; m.p. 180°–190° (dec.). The two crops combined; total 18.5 g (84.5%). A sample, 0.5 g was recrystallized from ethanol (25 ml) to give 0.2 g.; m.p. 185°–190° (dec.).

Anal. Calc'd. for $C_{16}H_{12}N_2O_2$: C, 49.97; H, 8.38; N, 19.42. Found: C, 50.16; H, 8.54; N, 19.17.

The yield of 6 was not affected when hydrazine hydrate was used. Crystalline 6 was also obtained when crude cis-epoxide (containing 8–10% trans-isomer) was used.

EXAMPLE 3

2,5-Dideoxystreptamine (7)

A. A solution of 17.7 g (122.5 mmole) of compound 6 in 100 ml glacial acetic acid and 2.0 g 10% Pd/C was hydrogenated on the Parr apparatus at 60° C and an initial pressure of 50 psi. After completion of the reaction (7 hrs.), the mixture was cooled to room temperature and filtered. The catalyst was washed with acetic acid and the washings were combined with the filtrate. The solution was colorless in the beginning but it turns brown on evaporation and exposure to the atmosphere. The acetic acid was removed by evaporation and the solid residue was stirred with 100 ml boiling ethanol. After cooling to room temperature, it was filtered and washed with icecold ethanol and dried to give 20.0 g of the acetate salt of 7, m.p. 205°–207° (dec.), (it becomes dark at 185°). The mother liquor, after evaporation to dryness was treated with 30 ml ethanol as above to give 3.0 g more of the acetate salt of 7. Both crystalline crops were combined, 27.0 g (78%). The mother liquor, after evaporation gave 5.5 g sticky residue of dark brown color.

Anal. Calc'd. for $C_{10}H_{22}N_2O_6.H_2O$: C, 42.24; H, 8.51; N, 9.85. Found: C, 43.14; H, 8.64; N, 10.00.

B. Conversion of the bis-acetate salt to the free amine (7)

A solution of 28.4 g (100 mmole) of the bis-acetate salt in 75 ml water was introduced into an anion-exchange column (Rexyn 201, OH form, 220 g) and the solution drained into the column until it reached the surface of the bed. It was rinsed 2–3 times with little water to force the solution down the column and then the column was washed with 600 ml distilled water (1.65 bed volumes, 1 hr). The effluent was tested with pH paper and was collected when the pH was above 7.0 (after 150 ml effluent). The effluent was evaporated to dryness to give 16.3 g (quantitative) crystalline amine 7, m.p. 173–180 (it turns brown at 165°). A sample of the amine 7, 2.7 g., was recrystallized from water (2 ml), ethanol (25 ml) to give 1.95 m.p.: it turns brown at 165°, it melts at 182°–183° (monohydrate), re-solidifies and melts at 198°–199°.

Anal. Calc'd. for $C_6H_{14}N_2O_2.H_2O$: C, 43.88; H, 9.82; N, 17.06. Found: C, 43.91; H, 9.95; N, 17.13.

EXAMPLE 4 dl-N-Carbethoxy-2,5-Dideoxystreptamine (8)

A solution was 54.0 g (329 mmole) of compound 7 in 270 ml water was diluted with 180 ml methanol (R.G.) and stirred and cooled in an ice-bath. Ethylchloroformate, 37.4 g (345 mmole) was added dropwise and at such a rate as to keep the inside temperature at 4°–6° C.

After the addition, 45 mins., stirring at 4°–6° C continued for 1 (heated hour and then at room temperature for 1 hour more. The solvent was removed by evaporation a rate 55°–60°) and the traces of water 200 removed by co-evaporation with ethanol (3 × 100 ml). The partly solidified residue was a mixture of the hydrochloride of 8, the bis-hydrochloride of 7 and the bis-carbethoxy compound 9. A sample was alkalified and examined by TLC (silica, 10% MeOH-ethylacetate, sprayed with HClO₄) shows two spots with Rf 0.34 (9) and Rf O (7 and 8).

The crude product was boiled and stirred with ethanol (absolute) for 5–10 mins., then cooled to room temperature and the insoluble bis-hydrochloride of 7 was removed by filtration and washed on the funnel with hot ethanol (2 × 50 ml) to give 14.0 g crystallized product. The combined filtrate and washings were evaporated to dryness and the sticky residue dissolved with water and extracted continuously with ethylacetate until all the bis carbethoxy compound 9 was removed (48 hrs.). The ethylacetate extract was evaporated to dryness to give 21.7 g (22.8%) crystalline 9; m.p. 204°–205°.

Anal. calc'd. for $C_{12}H_{22}N_2O_6$: C, 49.64; H, 7.64; N, 9.65. Found: C, 49.58; H, 7.70; N, 9.61

The aqueous phase containing the hydrochloride of 8 was decolorized with charcoal and evaporated to dryness and the traces of water were removed by coevaporation with ethanol (3 × 100 ml). The sticky residue was dissolved with boiling ethanol (200 ml) and after cooling to room temperature, was diluted with ether (100 ml) and cooled in the ice. The precipitate bishydrochloride of 7 was removed by filtration (2.5 g) and the filtrate evaporated to dryness to give 43.1 g (52%) of hydrochloride of 8 as a dry-foam. Conversion of the hydrochloride of 8 to the free base 8. Rexyn 201 (220 g) was packed into a column and washed with 6% NaOH (1.5l) to convert to OH form and then washed with distilled water until the effluent was neutral. The size of the column bed was 37.5 cm × 3.5 cm I.D. A solution of 35.0 g (137.5 mmole) of the hydrochloride of 8 in 50 ml water was introduced into the column and then the column was eluted with distilled water at a rate of 1.5 l/hour. (A fast elution was important since prolonged contact with the resin resulted in conversion of 8 to 1,3-cyclic urea). The first 175 ml of effluent was neutral and discharged. The following 400 ml had a pH >7.0 and was evaporated to dryness (at 40°–45° C) to give 28.8 g (96%) of crystalline amine 8. TLC (silica, 10% water in ethanol, developed with iodine) shows one spot Rf 0.29 and a trace of a spot with Rf O. This material was pure enough and was used for the resolution of the two optical isomers. A sample of 1.0 g was recrystallized from ethanol (2 ml) - ether (4 ml) and gave 0.7 g of analytical sample, m.p. 132°–134°.

Anal. calc'd. for $C_9H_{18}N_2O_4$: C, 49.51; H, 8.31; N, 12.83. Found: C, 49.34; H, 8.35; N, 12.80.

EXAMPLE 5

Resolution of
dl-N-carbethoxy-2,5-Dideoxystreptamine (8)

Compounds 10 and 11

A warm solution of 20.0 g (91.5 mmole) of compound 8 in 100 ml 95% ethanol-water was added to a warm solution of 12.38 g (45.8 mmole) (-)-2-nitrotartranilic acid [T. A. Montzka, T. L. Pindell and J. D. Matiskella, J. Org. Chem. 33, 3993 (1968)] in 100 ml 95% ethanol water and the solution allowed to crystallize at room temperature. Soon a crystalline precipitate formed. In some experiments the crystalline precipitate was accompanied with a jelly-like precipitate. In such a case, the mixture was heated to dissolve the jelly (the crystalline material remained undissolved) and then allowed to stay at room temperature overnight. The crystalline salt was filtered, washed with absolute ethanol (40 ml) and dried to give 19.2 g (86%); m.p. 195°–9° C (dec.), $[\alpha]_D^{25}$ –45.4 (1.0, $H_2O$). The rotation corresponds to a 94% optical purity. A sample was dissolved with boiling water-ethanol -ethanol mixture (1:1, 3 ml/g) and diluted with absolute ethanol (13.5 ml/g) and allowed to crystallize at room temperature. Two more recrystallization from the same system afforded the analytical sample m.p. 207°–208°, $[\alpha]_D^{25}$ –43.4 (1.0, $H_2O$); identified as compound 10.

Anal. calc'd. for $C_{19}H_{28}N_4O_{11}$: C, 46.71; H, 5.77; N, 11.50. Found: C, 46.50; H, 5.84; N, 11.52.

The mother liquor containing the other optical isomer mainly as a free base (some salt, 6–7 mmole, is also present) was evaporated to dryness at 40° and the residue was dissolved with 35 ml water. Rexyn 201, 15 ml (converted to the free base by washing with 4 bed volumes of 6% NaOH and then with distilled water was added and shaken for 2–3 minutes. It was filtered, the resin was washed with water (2× 10 ml) and the combined filtrate and washings evaporated to dryness at 40° to give a solid residue, 10.2 g. It was dissolved in 90 ml 95% EtOH-$H_2O$ and added to a warm solution of 10.8 g (40 mmole) (+) 2-nitrotartranilic acid in 90 ml 95% EtOH-$H_2O$ and the solution was allowed to crystallize at room temperature overnight. Filtered, washed on the funnel with absolute EtOH (40 ml) and dried to give 17.4 g, m.p. 207°–208° (dec.) $[\alpha]_D^{25}$ + 43.36 (1.0, $H_2O$). This rotation corresponds to optically pure product. A sample was recrystallized twice from 90% EtOH-$H_2O$ and had m.p. 207°–208° (dec.) $[\alpha]_D^{25}$ + 43.3 (1.0, $H_2O$), identified as compound 11.

Anal. Calc'd. for $C_{19}H_{28}N_4O_{11}$: C, 46.71; H, 5.77; N, 11.50. Found: C, 47.06; H, 5.84; N, 11.51.

EXAMPLE 5A

Conversion of the 2-Nitrotartranilate salts to the free bases 10 and 11.

A. Compound 11.

A column ws packed with Rexyn 201 (200 g) and washed with 6% NaOH (1.5l) to convert to OH form and then distilled water until the effluent was neutral. The size of the column was 34.5 cm × 3.4 cm I.D. A solution of 44.0 g (90 mmole) of (+)-2-nitrotartranilate diastereoisomer salt $[\alpha]_D^{25}$ + 43.3) in 70 ml water (heted to dissolve and cool to room temperature) was introduced and then the column was washed with water at arate of 3 l/hr. (15 mins.). The first 200 ml effluent was neutral to pH paper and discharged. The following 600 ml of colorless effluent (pH > 7.0) contained the material (at slower rates of elution, the effluent was yellow colored due to decomposition of the 2-nitrotartranilic acid by the resin. Prolonged conduct with the resin results in formation of 1,3-cyclic urea). The solution was evaporated to dryness at 40°–45° cooling the received with ice-ethanol mixture to speed up the evaporation process (higher temperature and prolonged heating at 45° results in urea formation). The residue, after co-evaporation with ethanol to remove traces of water was crystalline. Yield 18.2 g (93%), $[\alpha]_D^{25}$ – 37.6

(1.0 H₂O), m.p. 154°–6° (EtOH-ether, 1:10) of compound 11.

B. Compound 10

A solution of the (-)-2-nitrotartranilate diastereoisomer salt ($[\alpha]_D^{25} - 43.7$) in 70 ml water was passed through the column described in step A to yield 14.6 g (99%) of compound 10; m.p. 154°–6° (ethanol-ether, 1:10) $[\alpha]_D^{25} + 37.3$ (1.0, H₂O).

EXAMPLE 6 l-1N-Carbophenoxy-6N-Carbethoxy-2,5-dideoxystreptamine (12)

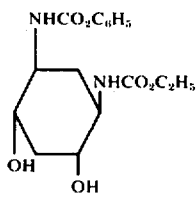

To a solution of 8.44 g (38.6 mmole) of compound 11 ($[\alpha]_D^{25}$–37.6) in 40 ml water was added 3.70 g (44 mmole) NaHCO₃ with stirring (mechanical stirrer) until dissolved. Acetone (R.G.) 40 ml was added and the solution was cooled in an ice bath. Phenylchloroformate, 6.73 g (43 mmole) was added portionwise, (10 mins.) with stirring, and then the mixture was stirred with cooling for 1 hr. A white precipitate formed. The mixture was diluted with 80 ml water and after stirring for 5 – 10 mins., it was filtered. The filtrate was kept aside. The solids were washed on the funnel with water (2 × 30 ml) and the washings were discharged. The crystalline material was dried first in the atmosphere and then in a vacuum dessicator overnight to give 10.6 g (81%) of crystalline; 12, m.p. 136°–141°, $[\alpha]_D^{25} + 6.0$ (1.0, EtOH). The filtrate was concentrated by evaporation at 35°–40° C. to about ¼ of the volume and 50 ml water added. The solids were separated by filtration and after drying, gave 0.9 g of compound 12, increasing the yield to 11.5 (88.5%).

EXAMPLE 7 l-1,6-Carbamate-3N-carbethoxy-2,5-dideoxystreptamine (1″)

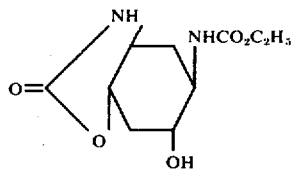

A mixture of 11.2 g (33.2 mmole) of compound 12 and 2.4 ml Et₃N in 90 ml., 90% acetone (R.G.) -water was stirred at room temperature. After 45 mins. stirring, the reaction mixture became a clear solution. After stirring for 5 hrs., 20 ml Dowex 50W – X4 (strongly acidic cation exchange resin, in the H⁺ form) previously washed with water several times and then washed with 90% acetone-water several times was added and stirred for 2–3 mins., to remove Et₃N. The mixture was filtered and the resin washed with 90% acetone-water (3 × 15 ml). The combined filtrate and washings were evaporated to dryness on the rotory evaporator at 40° – 45° C. To the solid residue, 15 ml acetone was added and stirred for 10 mins., then 50 ml ether was added and stirred for another 10 mins. and filtered. The solids on the funnel were washed with ether and dried in the atmosphere and then under vacuum (13 psi, 65° C) overnight* to give 7.5 g (92.5%) of compound 1″; m.p. 203°–205°. $[\alpha]_D^{25} - 58.5$ (1.0, H₂O).

*Drying under vacuum is required for complete removal of water. Before this treatment, the product shows a band for H₂O on NMR and the m.p. is less than 190°.

Anal. calc'd. for C₁₀H₁₆N₂O₅: C, 49.17; H, 6.60; N, 11.47. Found: C, 48.93; H, 6.48; N, 11.64.

EXAMPLE 8 d-1N-Carbophenoxy-6N-carboethoxy-2,5-dideoxystreptamine (13)

Substitution in the procedure of example 7 for the compound 11 used therein of compound 10 produced the title compound 13 in 91.5% yield; m.p. 135°–140° C; $[\alpha]_D^{25} - 6.7$ (1.0, EtOH).

EXAMPLE 9 d-1,6-Carbamate-3N-carbethoxy-2,5-dideoxystreptamine (1′)

Substitution in the procedure of example 7 for the compound 12 used therein of compound 13 produced the title compound 1′ in 92.5% yield; m.p. 203°–205° C; $[\alpha]_D^{25} + 57.4$ (1.0, H₂O).

Anal. calc'd. for C₁₀H₁₆N₂O₅: C, 49.17; H, 6.60; N, 11.47. Found: C, 49.13; H, 6.71; N, 11.47.

EXAMPLE 10

4-0-(6-Azido-2,3,4-tri-0-benzyl-6-deoxy-α-D-glucopyranosyl)-3N-carbethoxy-1,6-carbamoyl-2,5-dideoxystreptamine (14)

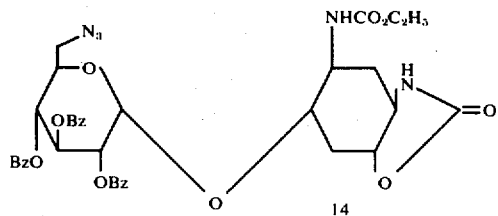

Into a flame-dry and nitrogen purged apparatus consisting of a 100 ml 3-neck flask, condenser, mechanical stirrer and nitrogen inlet and outlet tubes was added 2.44 g (10 mmole) of compound 1′ ($[\alpha]_D^{25} + 57.4$) and 15 ml dry DMF (dimethylformamide). The solution was placed under a slow stream of nitrogen, 5.5 g anhydrous calcium sulfate added and the mixture was stirred at room temperature for 30 mins., and then at 80° (oil bath temperature) for 15 mins. A solution of 5.1 g (10.3 mmole) of 6-Azido-2,3,4-tri-0-benzyl-6-deoxy-α-D-glucopyranosyl chloride in 5 ml dry DMF was added, followed by the addition of 6.3 g mercuric cyanide. The mixture was heated at 80° under nitrogen with stirring for 17 hours. Fresh mercuric cyanide, 3.0 g., was added and the mixture heated at 87° for 6 hours more. After cooling to room temperature, it was diluted with CHCl₃ (150 ml) and filtered. The cake was washed with CHCl₃ (2×10 ml). The combined filtrate and washings were washed with water (5 × 100 ml) dried and evaporated to dryness to give a dark brown sticky residue. TLC (silica, 5% methanol-CHCl₃ developed with HClO₄) shows five spots with Rf 0, 0.28

(major, 14), 0.5 and 0.92. It was dissolved in 20 ml CHCl₃ and added dropwise with stirring into 175 ml petroleum ether (b.p. 40° - 60°). The petroleum ether phase was decanted and the residue was dissolved in 20 ml CHCl₃ and again added to petroleum ether (175 mmol). The petroleum ether phase was decanted and combined with that above. The insoluble residue, 4.1 g, shows on TCL one major spot Rf 0.28 (14) and two minor with Rf 0 and 0.38. The petroleum ether phase shows on TLC a small spot for compound 14 and the spots with Rf 0.38, 0.5 and 0.92. On standing at room temperature overnight, 200 mg. of compound 14 was precipitated. It was separated and combined with that above to give a total of 4.3 g. The material was dissolved in CHCl₃ (10 ml) and added to the top of a column packed with 45 g silica Act. II (6.5 cm × 4.3 cm I.D.) and then washed with 250 ml 10% MeOH CHCl₃. This treatment removes the impurity with Rf O. The brown filtrate was evaporated to dryness to give 3.75 g (53.5%) of sticky residue. TLC shows one major spot for the title product and traces of a compound with Rf 0.38. This material was used in the next step without further purification. An analytical sample of compound 14 was obtained by crystallization and recrystallization from ether; m.p. 75°–85°; $[\alpha]_D^{25}$ + 87.4 (1.0, CHCl₃).

Anal. calc'd. for $C_{37}H_{43}N_5O_9$: C, 63.32; H, 6.18; N, 9.98. Found: C, 63.35; H, 6.14; N, 9.83.

EXAMPLE 11

4-0-(6-Azido-2,3,4-tri-0-benzyl-6-deoxy-α-D-glucopyranosyl)-N,N'-diethoxycarbonyl-2,5-dideoxystreptamine.

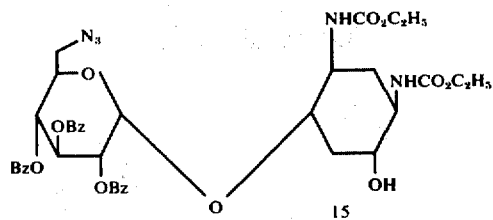

To a solution of 3.75 g crude 14 from the above preparation in 30 ml absolute ethanol was added 20 mg 55% NaH in oil suspension and the mixture refluxed for 3 hrs. with protection from moisture. After cooling to room temperature, acetone (35 ml) was added to dissolve the solids and the solution was neutralized by passing through a column containing 4.0 g Amberlite IR-120 (H⁺ form, washed with water and EtOH). The neutral solution was evaporated to dryness. TLC on silica [benzene-MEK (methyl ethyl ketone), 2:1] shows one major spot Rf 0.39 (15) and four minor with Rf 0,0.72, 0.89 and 1.0. It was chromatographed through a column packed with 100 g silica Act. II (14.5 cm × 4.0 cm I.D.) and eluted with benzene-MEK (2:1). Fraction of 20 ml were collected. The material came out in tubes 6–20. It was evaporated to dryness and the residue was boiled with 20 ml ethanol and filtered to remove some insoluble solids. The filtrate was evaporated to dryness to give 2.8 g (70%) of crystalline compound 15. Recrystallization from ethylacetate (10 ml)-petroleum ether (20 ml) gave 2.4 g; m.p. 166°–168° C., $[\alpha]_D^{25}$ + 77.4 (1.0, CHCl₃)

Anal. calc'd. for $C_{39}H_{49}N_5O_{10}$: C, 62.63; H, 6.60; N, 9.36. Found: C, 62.28, H, 6.54; N, 9.04.

EXAMPLE 12

4-0-(6-Azido-2,3,4-tri-0-benzyl-6-deoxy-α-D-glucopyranosyl)-6-0-(3-acetamido-2,4,6-tri-0-benzyl-3-deoxy-α-D-glucopyranosyl)-N-N'-diethoxycarbonyl-2,5-dideoxystreptamine (16)

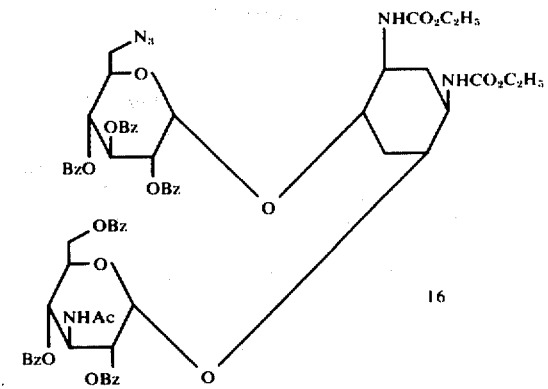

Into a flame-dry and nitrogen purged 50 ml 3-neck flask fitted with mechanical stirrer, condenser and nitrogen inlet and outlet tubes was added 2.99 g (4 mmole) compound 15 (m.p. 166°–168°) and 10 ml dry DMF and the mixture stirred at room temperature under a low stream of nitrogen to dissolve. Anhydrous calcium sulfate, 3.0 g was added and the mixture was stirred at room temperature for 30 mins. Then, 1.31 g (4.0 mmole) of 3-Acetamido-2,4,6-tri-0-benzyl-3-deoxy-α-D-glucopyranosyl chloride (compound XX) was added followed by addition of 3.0 g powder mercuric cyanide and the mixture was placed in an oil bath at 80° C and stirred under nitrogen. After 9 hrs., 1.31 g of XX and 1.5 g Hg (Cn)₂ was added, stirred at 80° for 12 hrs and then again 1.0 g of XX and 1.0 g Hg(CN)₂ added and stirred for 22 hrs. more (80° C). After cooling to room temperature, it was diluted with CHCl₃ (150 ml), filtered and the solids washed with CHCl₃ (2 × 10 ml). The combined filtrate and washings were washed with water (5 × 150 ml), dried and evaporated to dryness. TLC (alumina, 2% MeOH-CHCl₃) shows one major spot Rf 0.51 (compound 16) and four minor with Rf 0.17, 0.27 and 0.76. The sticky residue on treatment with ethyl acetate-ether crystallized. It was chromatographed through a column packed with alumina Act. II (150 g) having a bed 21.5 cm × 2.8 cm I.D. The column was eluted with 1% MeOH-CHCl₃ and fractions of 20 ml. were collected. Tubes 6–17 after evaporation gave 4.7 g of colorless sticky residue, which on TLC shows one major spot for 16 and a minor with Rf 0.76. It was boiled with ethylacetate (40 ml) and filtered to remove an insoluble solid (220 mg). The filtrate was evaporated to dryness, dissolved wih 15 ml boiling ethylacetate and diluted with 30 ml ether. After standing at room temperature overnight, the crystalline product 16 was filtered to give 3.40 g (70%); m.p. 178°–188°.

Anal. calc'd. for $C_{68}H_{80}N_6O_{15}$: C, 66.87; H, 6.60; N, 6.88. Found: C, 67.28; H, 6.67; N, 6.57.

EXAMPLE 13

4-0-(6-Acetamido-2,3,4-tri-0-benzyl-6-deoxy-α-D-glucopyranosyl)-6-0-(3-acetamido-2,4,6-tri-0-benzyl-3-deoxy-α-D-glucopyranosyl)-N,N'-diethoxycarbonyl-2,5-dideoxystreptamine (17)

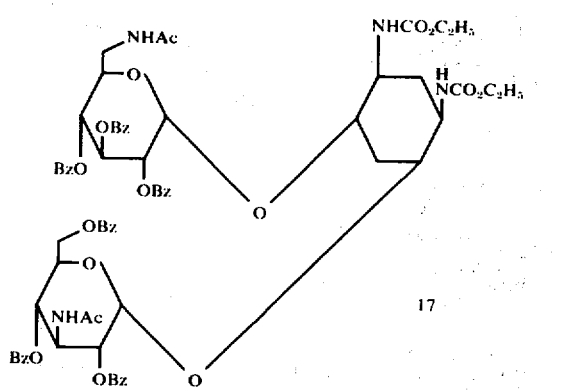

A mixture of 3.0 g (2.46 mmol) of 16 (m.p. ½°–188°) in 100 ml 90% EtOH water and Raney nickel catalyst was hydrogenated in the Paar apparatus at room temperature and an initial pressure of 55 psi. After 3 hrs., the reaction mixture was filtered and the catalyst washed with EtOH. The combined filtrate and washings was evaporated to dryness to give 2.77 g (94.5) of a syrup which solidified. I.R. (infrared) confirm the completion of the reaction (no $N_3$ bond). TLC on silica (10% MeOH-$CHCl_3$) shows one major spot Rf 0.43 and four minor ones. The material was dissolved in dry-pyridine (10ml), and acetic anhydride (1.5 ml) was added. After standing at room temperature for one hr., water (0.5 ml) was added to decompose the excess anhydride (15 mins., room temperature), then diluted with $CHCl_3$ (150 ml) and washed first with water (3 × 100 ml.), then with 5% HCl (100 ml) and finally with water (100 ml) and dried. After removal of the solvent by evaporation, the sticky residue was treated with boiling ethylacetate (25 ml) and the crystalline product 17 was filtered to give 1.95 g (67%); m.p. 210° – 213°. Recrystallization from EtOH produced an analytical sample; m.p. 217–218°.

Anal. calc'd. for $C_{70}H_{84}N_4O_{16}$: C, 67.96; H, 6.84; N, 4.53. Found: C, 68.09; H, 6.90; N, 4.57.

EXAMPLE 14

4-0(6-Acetamido-6-deoxy-α-D-glucopyranosyl)-6-0-(3-acetamido-3-deoxy-α-D-glucopyranosyl)-N,N'-diethoxycarbonyl-2,5-dideoxystreptamine (18)

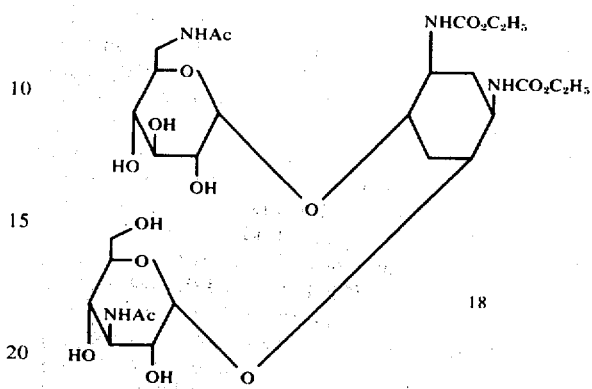

A mixture of 700 mg. of compound 17 and 400 mg 10% Pd/C in 80 ml 95% ethanol water was hydrogenated at room temperature and atmospheric pressure for 24 hrs. The reaction mixture was filtered and the catalyst washed with boiling 70% EtOH-water (4 × 15 ml). The combined filtrate and washings were evaporated to dryness to give 360 mg. crystalline material 17; m.p. 260°–262° (dec.).

Anal. calc'd. for $C_{28}H_{48}N_4O_{16}$: C, 48.27; H, 6.94; N, 8.04. Found: C, 47.53; H, 6.84; N, 7.64.

EXAMPLE 15

5-Deoxykanamycin A (19)

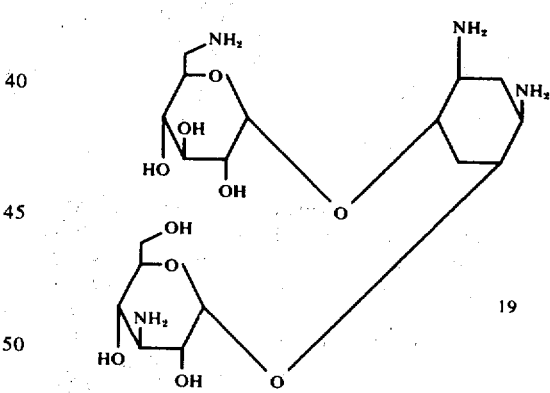

A solution of 360 mg (0.515 mmol) 18 in 20 ml 1N aqueous barium hydroxide was protected from atmospheric carbon dioxide and heated with stirring at 80° for 17 hrs. and at the refluxing temperature for 24 hours. It was then diluted with 30 ml. water and neutralized with $CO_2$. It was heated to boiling and filtered and the solids washed with boiling water (3 × 30 ml). The filtrate and washings were combined, 5 ml. of 1N $H_2SO_4$ was added to precipitate the $Ba^{++}$ from the water soluble $Ba(OAc)_2$ and filtered. The filtrate was passed through a column containing 10 g Rexyn 201 (strong basic resin in the OH form) to remove the acids ($H_2SO_4$ and AcOH) and evaporated to dryness to give 200 mg. sticky residue. TLC on silica ($H_2O$-MeOH-$NH_4OH$-$CHCl_3$, 1:4:2:1, sprayed with ninidrin) shows two spots with Rf 0.19 (compound 19) and Rf 0.49. The material was chromatographed from a column packed with Rexyn 102 (NH$_4^+$ form) having a bed 0.9 cm ID × 12.0 cm. The column was eluted first with water (100 ml), then with 0.1N ammonium hydroxide (200 ml) and then with 1N ammonium hydroxide (300 ml). The last fraction, after evaporation to dryness, gave 140 mg of 19. TLC shows one spot and NMR shows the absence of NAc and NCO$_2$Et groups. Treatment with ethanol gave 19 as a crystalline material.

We claim:

1. A process for the preparation of the compound having the formula

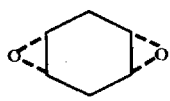

which process comprises the oxidizing of 1,4-cyclohexadiene with m-chloroperbenzoic acid in a temperature range of about −10° C. to about +35 ° C to produce a mixture of cis-and trans- bisepoxides in a ratio of about 2:1, respectively, and separating the cisbisepoxide from the mixture.

2. A process of claim 1 for the preparation of cis-1,4-cyclohexadiene dioxide wherein the oxidation is conducted wtih a ratio of about 1 mole of diene per two to three moles of peracid in a reaction inert organic solvent selected from the group consisting of methylene chloride, dichloroethane, chloroform, benzene, hexane, toluene, diethylether and dioxane with stirring for at least 3 hours.

3. The process of claim 2 for the preparation of cis-1,4-cyclohexadiene dioxide wherein the oxidation is conducted with a ratio of about 1 mole of diene per two moles of m-chloroperbenzoic acid at about 0° C. to about +10° C. for at least 3 hours with stirring.

* * * * *